US009615835B2

(12) United States Patent
Lam et al.

(10) Patent No.: US 9,615,835 B2
(45) Date of Patent: Apr. 11, 2017

(54) DRILL ATTACHMENT FOR CANNULATED SURGICAL DRILLS

(71) Applicant: British Columbia Cancer Agency Branch, Vancouver (CA)

(72) Inventors: Lok Tin Lam, Coquitlam (CA); Scott Elton Young, Vancouver (CA); Derek Thong, Vancouver (CA)

(73) Assignee: BRITISH COLUMBIA CANCER AGENCY BRANCH, Vancouver (CA)

( * ) Notice: Subject to any disclaimer, the term of this patent is extended or adjusted under 35 U.S.C. 154(b) by 0 days.

(21) Appl. No.: 14/440,839

(22) PCT Filed: Nov. 14, 2013

(86) PCT No.: PCT/CA2013/050870
§ 371 (c)(1),
(2) Date: May 5, 2015

(87) PCT Pub. No.: WO2014/075184
PCT Pub. Date: May 22, 2014

(65) Prior Publication Data
US 2015/0297245 A1 Oct. 22, 2015

Related U.S. Application Data

(63) Continuation-in-part of application No. PCT/CA2012/050807, filed on Nov. 14, 2012.

(51) Int. Cl.
*B23B 45/02* (2006.01)
*A61B 17/16* (2006.01)
(Continued)

(52) U.S. Cl.
CPC ........ *A61B 17/1624* (2013.01); *A61B 17/162* (2013.01); *A61B 17/1637* (2013.01);
(Continued)

(58) Field of Classification Search
CPC ..... B25D 11/106; B25D 11/10; B25D 11/102; B25D 16/003; B25D 23/0035;
(Continued)

(56) References Cited

U.S. PATENT DOCUMENTS 2,328,270 A * 8/1943 Greenberg ........... B25D 11/106
15/22.2
2,724,573 A * 11/1955 Lundquist ............ B25D 11/106
173/205

(Continued)

FOREIGN PATENT DOCUMENTS

CA 1090169 A1 11/1980
CN 2662839 Y 12/2004
(Continued)

OTHER PUBLICATIONS

International Search Report and Written Opinion for counterpart International Patent Application No. PCT/CA2012/050807 mailed Jul. 31, 2013.
(Continued)

*Primary Examiner* — Andrew M Tecco
(74) *Attorney, Agent, or Firm* — Maschoff Brennan

(57) ABSTRACT

A hammer drill attachment is provided for attachment to a bi-directional surgical drill. The attachment comprises a lengthwise adapter to engage a chuck of the surgical drill, a transmission mechanism, and a quick-release mechanism. The transmission mechanism comprises a pair of toothed plates, the teeth of a proximal plate configured to permit engagement with the teeth of a distal plate. When the proximal plate rotates in a first direction, the proximal plate transmits a rotational motion to the distal plate. When the proximal plate rotates in a second direction, the proximal plate transmits an axial percussive force to the distal plate. The quick-release mechanism comprises a socket to receive a collet, a socket seater, and a latching arm to move the
(Continued)

socket seater with respect to the socket, thereby seating or unseating the collet in the socket.

18 Claims, 8 Drawing Sheets

(51) Int. Cl.
*A61B 17/84* (2006.01)
*A61B 17/86* (2006.01)
*B23B 45/00* (2006.01)

(52) U.S. Cl.
CPC ........ *A61B 17/1662* (2013.01); *A61B 17/844* (2013.01); *A61B 17/8625* (2013.01); *A61B 17/8685* (2013.01); *B23B 45/005* (2013.01)

(58) Field of Classification Search
CPC . B25D 21/007; A61B 17/1624; A61B 17/162; Y10T 408/957; Y10T 403/70
See application file for complete search history.

(56) References Cited

U.S. PATENT DOCUMENTS

| | | | |
|---|---|---|---|
| 3,006,202 A * | 10/1961 | Moorhead | B25D 11/106 173/203 |
| 3,371,725 A | 3/1968 | Jansen et al. | |
| 3,650,336 A | 3/1972 | Koehler | |
| 3,774,699 A | 11/1973 | Schmuck | |
| 4,098,351 A | 7/1978 | Alessio | |
| 4,222,443 A | 9/1980 | Chromy | |
| 4,450,919 A * | 5/1984 | Cousineau | B25D 17/005 173/29 |
| 4,489,792 A * | 12/1984 | Fahim | B25D 11/106 173/29 |
| 4,491,443 A | 1/1985 | DeCaro | |
| 4,605,348 A | 8/1986 | DeCaro | |
| 4,998,589 A | 3/1991 | Wiesendanger | |
| 5,476,467 A | 12/1995 | Benoist | |
| 5,494,115 A * | 2/1996 | Hwong | B25D 11/106 173/13 |
| 5,741,253 A | 4/1998 | Michelson | |
| 5,806,609 A | 9/1998 | Stock et al. | |
| 5,816,341 A | 10/1998 | Bone et al. | |
| 5,820,312 A * | 10/1998 | Stock | B25D 16/00 173/205 |
| 5,899,425 A | 5/1999 | Corey, Jr. et al. | |
| 5,993,454 A * | 11/1999 | Longo | A61B 17/1624 606/80 |
| 5,996,454 A | 12/1999 | Brinks, Jr. | |
| 6,044,918 A | 4/2000 | Noser et al. | |
| 6,110,174 A | 8/2000 | Nichter | |
| 6,209,886 B1 | 4/2001 | Estes et al. | |
| 6,286,611 B1 | 9/2001 | Bone | |
| 6,557,648 B2 | 5/2003 | Ichijyou et al. | |
| 6,684,964 B2 | 2/2004 | Ha | |
| 6,976,545 B2 | 12/2005 | Greitmann | |
| 7,059,425 B2 | 6/2006 | Ikuta | |
| 7,096,972 B2 | 8/2006 | Orozco, Jr. | |
| 7,124,839 B2 | 10/2006 | Furuta et al. | |
| D537,940 S | 3/2007 | Büttler | |
| 7,506,693 B2 | 3/2009 | Stirm | |
| 7,513,317 B2 | 4/2009 | Satou | |
| 8,157,021 B2 * | 4/2012 | Chen | B23B 31/1071 173/29 |
| 2002/0056558 A1 | 5/2002 | Bongers-Ambrosius et al. | |
| 2002/0170186 A1 | 11/2002 | Sakaguchi | |
| 2003/0229351 A1 | 12/2003 | Tidwell et al. | |
| 2004/0011565 A1 * | 1/2004 | Lyon | E21B 10/36 175/296 |
| 2004/0050568 A1 | 3/2004 | Orozco, Jr. | |
| 2005/0031424 A1 | 2/2005 | Hernandez, Jr. et al. | |
| 2005/0199407 A1 | 9/2005 | Hermann | |
| 2006/0201688 A1 | 9/2006 | Jenner et al. | |
| 2006/0237205 A1 | 10/2006 | Sia et al. | |
| 2007/0056756 A1 | 3/2007 | Chung et al. | |
| 2008/0181740 A1 | 7/2008 | Waitszies | |
| 2010/0204613 A1 | 8/2010 | Rollins et al. | |
| 2013/0161042 A1 | 6/2013 | Blum et al. | |
| 2013/0161043 A1 | 6/2013 | Blum et al. | |
| 2014/0182870 A1 | 7/2014 | Herr | |
| 2014/0309636 A1 | 10/2014 | Meek et al. | |
| 2015/0038970 A1 | 2/2015 | Coope | |

FOREIGN PATENT DOCUMENTS

| | | |
|---|---|---|
| EP | 0078619 A2 | 5/1983 |
| EP | 1941838 A1 | 7/2008 |
| GB | 1123452 A | 8/1968 |
| GB | 1 494 553 A | 12/1977 |
| GB | 1584082 A | 2/1981 |

OTHER PUBLICATIONS

International Search Report and Written Opinion for counterpart International Patent Application No. PCT/CA2013/050870 mailed Feb. 20, 2014 (11 pages).
Extended European Search report for European Application No. 13854268.3 mailed on Aug. 9, 2016.

* cited by examiner

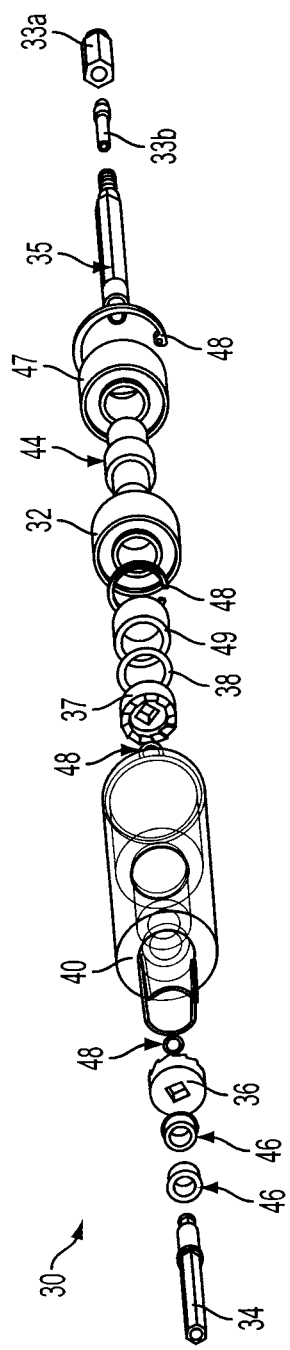
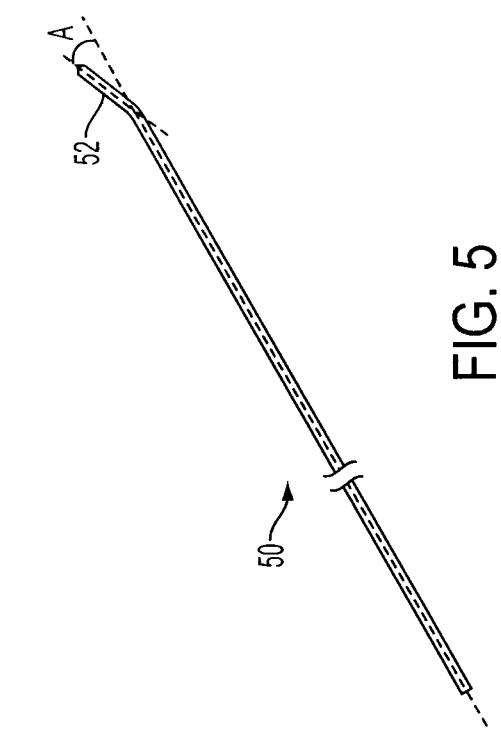
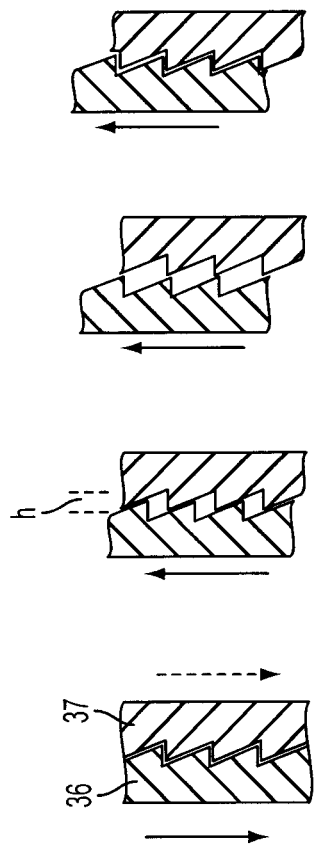

DRILL ATTACHMENT FOR CANNULATED SURGICAL DRILLS

CROSS-REFERENCE TO RELATED APPLICATION

The present application is a U.S. National Stage Application under 35 U.S.C. §371 of International Application Serial No. PCT/CA2013/050870, filed on Nov. 14, 2013, which claims priority as a continuation-in-part to PCT/CA2012/050807, filed Nov. 14, 2012, the contents of which are incorporated herein by reference in their entireties.

BACKGROUND

The pelvis is a ring-like structure made up of three bones, the sacrum and two innominate bones that have three parts, the ilium, ischium, and pubis. The ring-like structure of the pelvic bones gives them great strength. Since the structure is ring-like, however, a fracture in one part of the structure will often be accompanied by another fracture or severe ligamentous injury at other points in the pelvic ring. Surgery is often required to repair the damage. Screws, bolts and metal plates facilitate the healing of the bones, and external fixators are common.

However, when external fixators are used, they may need to remain in place for as long as six to twelve weeks. Meticulous observation is required to spot signs of infection at the pin sites and note pins that are loosening and need to be replaced. Therefore, internal anchors are generally preferred. However, placing a plate on the bone requires a significant operation with resulting high blood loss. In some cases, a straight intramedullary screw may be placed along a curved path. While the screw is less invasive, because of the ring-shaped structure and curvature of the pelvic bones, the fixation may be inadequate because the straight screw cannot be implanted very far into a curved bone. This may result in inadequate fixation. Moreover, the screw must be relatively small in diameter to avoid extending through the bone. Surgically speaking, implanting a screw such that it extends from the bone can result in significant hazard to the patient because it may puncture or otherwise impinge upon important vascular and nervous structures.

Curved anchors and apparatus for forming curved holes for receiving the anchors can therefore be advantageous. Modified Kirschner wires having an angled distal tip may be driven into cancellous bone by a hammering action to form curved holes. Surgical drills provide only rotative motion in one or both directions of rotation and do not have a hammering capability. Therefore, in addition to a surgical drill, a hammering device or mechanism will also be needed during a fixation to drive the wire into the bone.

In order to simplify the tools, and/or the number of tools required by a surgeon for fixing bone fractures where curved fixation paths are required, there remains a need for an attachment device for a bi-directional rotary drill, such as a surgical drill, to convert the rotary drill to a hammer drill for driving modified drill wires into bone to produce curved bores for accepting bone anchors for fixing curved bone portions.

SUMMARY

Presently disclosed is a hammer drill attachment that enables a rotary drill to be used to provide a hammering action. The hammer drill attachment may be provided individually or as part of a drill kit that also includes a rotary drill, and the attachment may be usable in surgical procedures requiring a surgical drill implement to be hammered into bone.

In an embodiment, a quick-release mechanism for a collet comprises a socket configured to receive the collet in a collet lumen, the socket comprising a proximal socket flange and a distal socket flange distal to the proximal socket flange. The quick-release mechanism further comprise a socket seater further comprising a socket lumen configured to receive the socket, a socket seater flange disposed between the proximal socket flange and the distal socket flange, and a socket seater stub. The quick-release mechanism further comprises a return spring disposed on an exterior surface of the socket seater, and a latching arm in contact with the socket seater stub, and having a first state, a second state, and a third state.

In an additional embodiment, a transmission mechanism, comprises a housing, a proximal toothed plate disposed within the housing and including a body having a distal side comprising a plurality of teeth, and a distal toothed plate disposed within the housing and including a body having a proximal side comprising a plurality of teeth configurable to engage the plurality of teeth of the proximal toothed plate. The housing of the transmission mechanism is configured to axially constrain the distal toothed plate. Each tooth of the proximal toothed plate and each tooth of the distal toothed plate comprises a riser side and a ramp side. Within the transmission mechanism, a rotation of the proximal toothed plate in a first direction engages the plurality of teeth of the proximal toothed plate with the plurality of teeth of the distal toothed plate, and a rotation of the proximal toothed plate in a second direction disengages the plurality of teeth of the proximal toothed plate from the plurality of teeth of the distal toothed plate and rotationally slides the plurality of teeth of the proximal toothed plate with respect to the plurality of teeth of the distal toothed plate thereby imparting an axial impact force to the distal toothed plate.

In a further embodiment, a drill attachment for a bi-directional drill may comprise a housing, a lengthwise adapter comprising a proximal end configured to engage a chuck of the bi-directional drill, a transmission mechanism configured to engage a distal end of the lengthwise adapter, and a quick-release mechanism for a collet. The transmission may comprise a proximal toothed plate disposed within the housing and including a body having a distal side comprising a plurality of teeth, and a distal toothed plate disposed within the housing and including a body having a proximal side comprising a plurality of teeth configurable to engage the plurality of teeth of the proximal toothed plate. The distal toothed plate may also be configured to axially receive a collet in a distal central structure thereof. The housing of the transmission mechanism may be configured to axially constrain the distal toothed plate. Each tooth of the proximal toothed plate and each tooth of the distal toothed plate comprises a riser side and a ramp side. Within the transmission mechanism, a rotation of the proximal toothed plate in a first direction engages the plurality of teeth of the proximal toothed plate with the plurality of teeth of the distal toothed plate, and a rotation of the proximal toothed plate in a second direction disengages the plurality of teeth of the proximal toothed plate from the plurality of teeth of the distal toothed plate and rotationally slides the plurality of teeth of the proximal toothed plate with respect to the plurality of teeth of the distal toothed plate thereby imparting an axial impact force to the distal toothed plate. The quick-release mechanism may include a socket configured to receive the collet in a collet lumen, the socket comprising a proximal socket flange and a distal socket flange distal to the proximal socket flange. The quick-release mechanism further comprise a socket seater further comprising a socket lumen configured to receive the socket, a socket seater flange disposed between the proximal socket flange and the distal socket flange, and a socket seater stub. The quick-release mechanism further comprises a return spring disposed on an exterior surface of the socket seater, and a latching arm in contact with the socket seater stub, and having a first state, a second state, and a third state.

In a further embodiment, a surgical drill kit comprises a bi-directional cannulated surgical drill and a drill attachment. The drill attachment for the bi-directional drill comprises: a housing; a lengthwise adapter comprising a proximal end configured to engage a chuck of the bi-directional drill; a transmission mechanism configured to engage a distal end of the lengthwise adapter, comprising comprises a proximal toothed plate disposed within the housing and including a body having a distal side comprising a plurality of teeth, and a distal toothed plate disposed within the housing and including a body having a proximal side comprising a plurality of teeth configurable to engage the plurality of teeth of the proximal toothed plate. The housing of the transmission mechanism is configured to axially constrain the distal toothed plate. Each tooth of the proximal toothed plate and each tooth of the distal toothed plate comprises a riser side and a ramp side. Within the transmission mechanism, a rotation of the proximal toothed plate in a first direction engages the plurality of teeth of the proximal toothed plate with the plurality of teeth of the distal toothed plate, and a rotation of the proximal toothed plate in a second direction disengages the plurality of teeth of the proximal toothed plate from the plurality of teeth of the distal toothed plate and rotationally slides the plurality of teeth of the proximal toothed plate with respect to the plurality of teeth of the distal toothed plate thereby imparting an axial impact force to the distal toothed plate. The drill attachment further comprises a quick-release mechanism for a collet comprises a socket configured to receive the collet in a collet lumen, the socket comprising a proximal socket flange and a distal socket flange distal to the proximal socket flange. The quick-release mechanism further comprise a socket seater further comprising a socket lumen configured to receive the socket, a socket seater flange disposed between the proximal socket flange and the distal socket flange, and a socket seater stub. The quick-release mechanism further comprises a return spring disposed on an exterior surface of the socket seater, and a latching arm in contact with the socket seater stub, and having a first state, a second state, and a third state.

BRIEF DESCRIPTION OF THE FIGURES

FIG. 3 depicts an exploded perspective view of the cannulated hammer drill attachment of FIG. 2 according to an embodiment.

FIGS. 4A-4D illustrate the engagement between transmission plates of a cannulated hammer drill according to an embodiment.

FIG. 5 depicts a Kirschner wire having a bent tip for producing curved holes in bone according to an embodiment.

DETAILED DESCRIPTION

Figure 1:
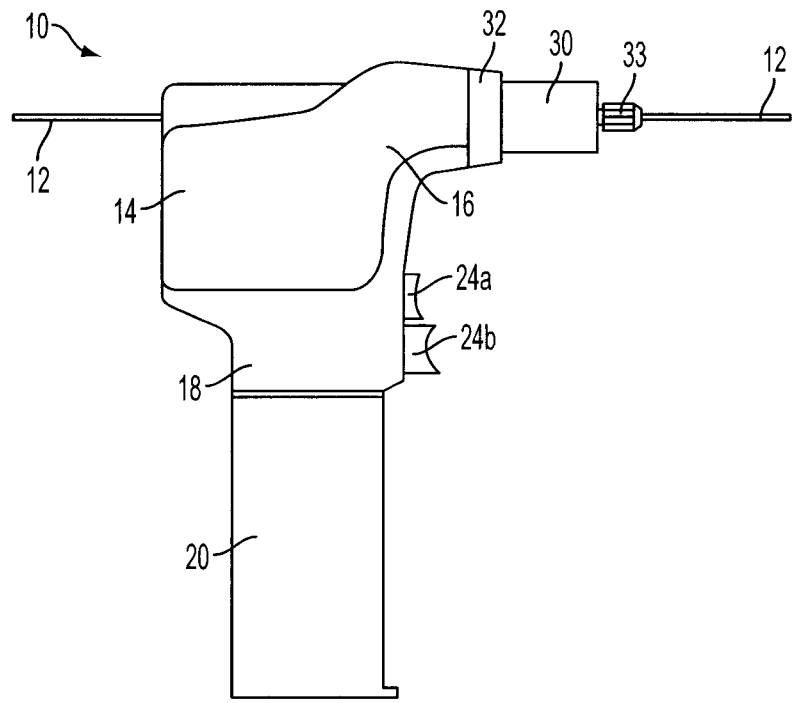
FIG. 1 depicts a cannulated surgical drill according to an embodiment.

The pelvic bones exhibit many areas of curvature. Fractures of the pelvic bones therefore may often require curved intramedullary anchors to fix the bones. However, to use curved anchors, the holes for receipt of the anchors must also be curved and typical drill arrangements do not allow for the formation of curved holes. Curved holes may be created by using a bent and sharpened tip on the end of a piece of flexible wire, and advancing the wire into the bone by a hammering action. The hammering action may be provided by a cannulated hammer drill system as described with reference to FIGS. 1-3, and the wire may have a configuration as depicted in FIG. 5.

Flexible drill wires, such as the wire 50 depicted in FIG. 5, which may be used to produce curved holes, may be formed from materials such as nitinol (nickel titanium) or spring tempered stainless steel, for example. Depending on the diameter desired for the hole, the wire 50 may have a diameter from about 0.5 mm to about 5 mm. In embodiments, the wire 50 may have a diameter of about 0.5 mm, about 0.75 mm, about 1.0 mm, about 1.25 mm, about 1.5 mm, about 1.75 mm, about 2.0 mm, about 2.5 mm, about 3.0 mm, about 3.5 mm, about 4.0 mm, about 5.0 mm, or any diameter between any two of the listed values. To enable the wire 50 to be advanced in a non-linear direction with respect to the longitudinal axis of the wire, the tip 52 of the wire may be bent at an angle from the longitudinal axis. The angled tip 52 may have a length of about 5 mm to about 12 mm extending from the end. In embodiments, the angled tip 52 may have a length of about 5 mm, about 6 mm, about 7 mm, about 8 mm, about 9 mm, about 10 mm, about 11 mm, about 12 mm, or any length between any of the listed values. The angled tip 52 may be bent from the longitudinal axis at an angle A of about 25° to about 35°. In embodiments, the angled tip 52 may be disposed at an angle A of about 25°, about 26°, about 27°, about 28°, about 29°, about 30°, about 31°, about 32°, about 33°, about 34°, about 35°, or any angle between any of the listed values. As an example, a drill wire 50 may be on the order of about 1.5 mm in diameter, and may include a bent tip 52 of about 10 mm in length at an angle A of about 30°.

A drill wire 50 may be advanced within the soft cancellous bone inside the pelvis by means of a hammering action. The bent tip 52 will cause the wire 50 to turn, or be directed off axis in the direction of the angled tip as the wire is advanced. If the wire 50 is able to be rotated to turn the tip 52 in any arbitrary orientation, the overall direction of the wire can be made to bend in the direction which is required. Straight paths may be approximated by alternately turning the tip 52 at 180° offsets and producing several short curved paths in opposing directions. A fluoroscope may be used to continuously monitor the position of the drill in the bone, and allow adjustments to be made as the hole is being formed. The process of producing curved holes within the pelvis is aided by the outer structure of hard cortical bone which can partially guide the wire within the softer cancellous bone of the pelvis.

To produce the hammering action needed to drive the drill wire 50 into bone, a hammer drill attachment 30 may be attached to a standard bi-directional surgical drill 10 as shown in FIG. 1.

With reference to FIG. 1, there is illustrated a surgical drill 10 which may be a cannulated drill configured for accepting a Kirschner wire 12 (also referred to as a "K-wire" or "K-pin") through the cannula thereof. The drill 10 may be a bi-directional drill, while use of a unidirectional drill may also be contemplated. Some examples of surgical drills are the MPower® and PowerPro® devices manufactured by ConMed Linvatec of Largo Fla.

With the inclusion of a cannulated hammer-drill attachment 30, discussed in more detail with reference to FIGS. 2 and 3, a surgical drill 10 may be adapted to drive the Kirschner pin 12 into the bone. If the pins 12 are configured as discussed with reference to wire 50 of FIG. 5, curved hole paths may be formed in the bone. Hammer-drill attachment 30 may be attached to the drill body by means of an attachment device 32. The drill 10 may also be used with other types of attachments, and some examples of additional attachments which may be used include, but are not limited to, keyless chucks, quick-connect drill attachments, reamers, sagittal saws, and reciprocating saws.

While a cannulated drill may have a variety of configurations, in general, a drill 10 may include a motor housing 14, a gear housing 16 forwardly thereof, a depending pistol-grip handle 18, and a removable battery pack 20 which may form a part of the pistol-grip handle. The handle 18 may be ergonomically designed and include a pair of triggers 24a, 24b projecting forwardly of the pistol-grip handle. In an embodiment, trigger 24a may provide a first, or forward direction of rotation, and trigger 24b may provide a second, or reverse direction of rotation. The triggers 24a, 24b may be variable speed triggers that provide control of the speed of rotation. The hammer-drill attachment 30 may include a rotary connection member, such as a collet 33, for engaging the K-wire 12 and rotating the K-wire with the rotation of the drill motor. During usage of such a configuration, a surgeon may control the operation of the drill (speed, direction of rotation, insertion or withdrawal) with one hand.

As depicted in FIG. 1, surgical drills, including cannulated surgical drills, may have two separate buttons to control direction, unlike conventional drills which generally have one trigger to run the drill and a separate bi-stable switch to control direction. The hammer drill attachment 30 of FIGS. 2 and 3 includes a clutch 32, which may be a unidirectional bearing, and which exploits the bi-directional design. This clutch bearing 32 allows the attachment to provide free rotation in a first direction of rotation, while inhibiting rotation in the opposite, second direction and allowing the rotation in the second direction to be converted into a hammering motion. The attachment 30 may have a housing 40 that retains the attachment parts and provides an attachment portion 42 to engage with and fixedly retain the housing on the drill to prohibit rotation of the housing upon operation of the drill.

Attachment 30 includes an input shaft 34 configured to receive rotary motion from an output member (not shown) of a rotary drill in each of the first direction of rotation and the second direction of rotation of the drill. Input shaft 34 rotates freely in both directions. Attachment 30 also includes an output shaft 35 configured for outputting rotary motion or pulsed axial percussions, and a transmission arrangement 31 connecting the input shaft with the output shaft. In an embodiment as depicted in FIGS. 2 and 3, the input shaft 34 and output shaft 35 are in axial alignment and are cannulated for receipt of a K-wire therethrough, and may therefore be used with cannulated surgical drills.

The transmission arrangement 31 is configured to transmit rotary motion from the input shaft 34 to the output shaft 35 during rotation of the input shaft in the first direction of rotation, and is also configured to convert rotary motion of the input shaft to pulsed axial percussions of the output shaft during rotation of the input shaft in the second direction of rotation. In an embodiment, the transmission arrangement 31 may include a first transmission member 36 disposed in conjunction with the input shaft 34 to receive corresponding rotary motion from the input shaft during rotation of the input shaft in each of the first direction of rotation and the second direction of rotation. The transmission arrangement 31 may also include a second transmission member 37 disposed in conjunction with the first transmission member 36 and the output shaft 35 to transfer the rotary motion of the first transmission member to the output shaft during rotation of the input shaft in the first direction of rotation, and convert the rotary motion of the first transmission member to pulsed axial percussions and transfer the pulsed axial percussions to the output shaft during rotation of the input shaft in the second direction of rotation.

The input shaft 34 has a first end configured to be connected to an output member of a drill and a second end spaced apart from the first end and disposed within the housing 40. The output shaft 35 has a first end disposed within the housing 40 adjacent the second end of the input shaft and a second end spaced apart from the first end. The first transmission member 36 may be fixedly attached on the second end of the input shaft 34 for rotation of the first transmission member with the input shaft, and the second transmission member 37 may be fixedly attached on the first end of the output shaft 35 for movement of the output shaft with the second transmission member. In the embodiment depicted in FIGS. 2 and 3, the first transmission member is configured as a saw-tooth disc 36, and the second transmission member is configured as a saw-tooth disc 37.

In an embodiment, at least one of the first transmission member and the second transmission member (corresponding with either 36 or 37 in the embodiment of FIG. 3) may be a disc-shaped member having a surface disposed towards the other of the first transmission member and the second transmission member. As shown in FIG. 3, the surface of the disc shaped member 36 or 37 may have a plurality of teeth disposed annularly about a central axis. As depicted in the representation presented by FIG. 4, the teeth may have a right-triangular cross-section in the annular direction with a face portion disposed at an angle to the surface and a leg portion disposed axially to the surface.

In an embodiment, the other of the first transmission member and the second transmission member (corresponding with the other of either 36 or 37 in the embodiment of FIG. 3) may be configured as an engagement device having at least one projection that is configured to engage with the leg portions of the teeth during rotation of the input shaft 34 in the first direction of rotation to rotate the second transmission member with the first transmission member, and glidingly move over the face portions of the teeth during rotation of the input shaft in the second direction of rotation to axially displace the output shaft 35 by an amount which is substantially the height of the teeth from the surface of the disc (see h in FIG. 4). A biasing member, which may be configured as a wave washer, such as wave washer 38 in FIG. 3, may be disposed to provide biased engagement between the teeth of the one transmission member and the at least one projection of the other transmission member.

Figure 2:
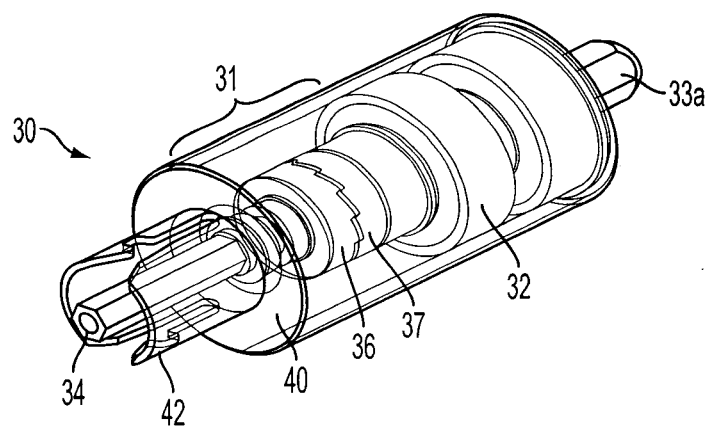
FIG. 2 depicts a perspective view of a cannulated hammer drill attachment according to an embodiment.

In the embodiment as depicted in FIGS. 2 and 3, both of the first and second transmission members 36, 37 may be saw-toothed disc members with a plurality of teeth disposed annularly about a central axis. As represented in FIG. 4, the teeth on the disc members 36, 37 may be complementary to one another. Upon movement of the disc member 36 in a first direction of rotation as represented by panel A of FIG. 4, the leg portions of the teeth of the first disc member 36 engage with the leg portions of the teeth of the second disc member 37 and rotate the second disc member with the first disc member. However, as represented by panels B-D of FIG. 4, upon rotation of the first disc member 36 in the opposite direction, since disc member 37 is prevented from rotating in the opposite direction by the uni-directional bearing 32, the teeth of the first disc member slide over the face portions of the teeth of the second disc member to axially displace the second disc member by an amount h corresponding to the height of the teeth. After the teeth pass over one another, the discs snap back together (panel D) and an axial hammering movement is created.

This axial displacement results in an axial displacement of the output shaft 35, and any surgical implement connected with the output shaft via the collet 33. In some designations, the term 'chuck' may be used interchangeably with the term 'collet.' A collet 33 may include an engaging member 33*b* through which the article to be retained is held, and an internally threaded cap 33*a* that may be threadable onto the end of the shaft 35 to compress the engaging member around the implement to be retained.

A unidirectional bearing 32 prohibits rotation of the second disc member 37 and shaft 35 in the second direction. A bushing 44 may be provided to allow for axial movement of the shaft 35 within the unidirectional bearing 32. Additional bearings 46, 47 may be provided as needed to guide rotation of the shafts 34, 35, and retaining rings 48 may be used to hold the various components in place within the housing and on the shafts. A spacer ring 49 may also be included to provide a bearing surface for the wave washer 38.

A hammer drill attachment 30 may be packaged and sold individually as an accessory for rotary drills, or alternatively may be included in a pre-packaged kit. A kit may include a drill, such as drill 10 of FIG. 1, as well as assorted attachment devices, such as the hammer drill attachment 30 or any of the previously mentioned attachments including keyless chucks, quick-connect drill attachments, reamers, sagittal saws, and reciprocating saws.

Figure 7:
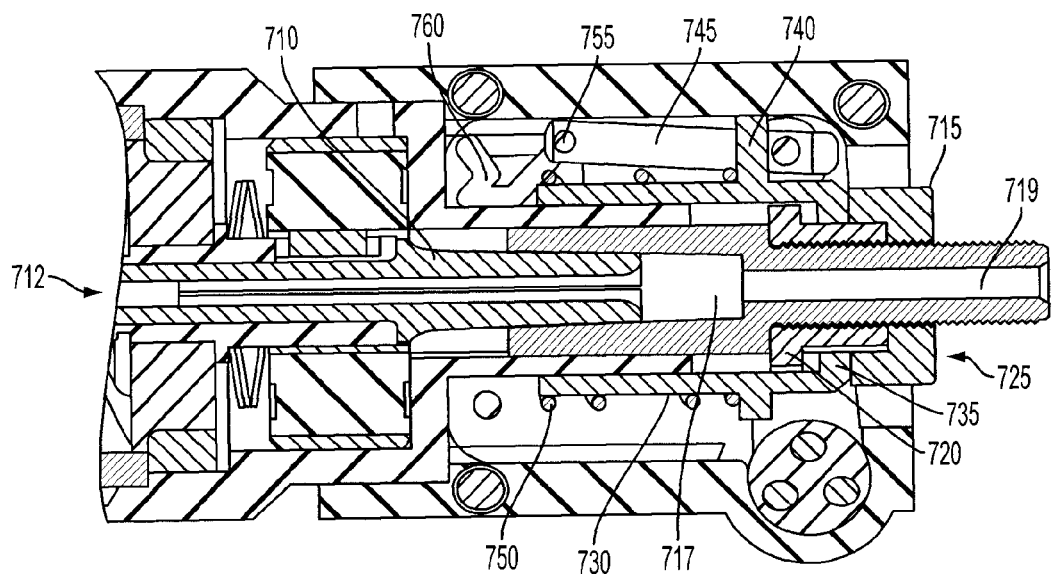
FIG. 7 depicts a quick-release mechanism for a Kirschner wire in a cannulated hammer drill attachment according to an embodiment.

The hammer drill attachment may be capable of reversibly securing the K-wire during surgery, while requiring minimal manipulation by the surgeon using the drill. A handle may be supplied to the drill attachment to permit the surgeon to lock the K-wire. However, it may be appreciated that the surgeon may not wish to apply a force to a handle for coupling the K-wire to the drill attachment throughout the entire surgical procedure. Rather, a surgeon may prefer to have a mechanism that readily engages the drill attachment to the K-wire that does not require constant attention during the surgery. FIG. 7 depicts an embodiment of a quick-release mechanism to allow a single action to a handle to engage the drill attachment to the K-wire, and a separate single action to disengage the drill attachment.

The quick-release mechanism depicted in FIG. 7 includes a collet 710 disposed near a socket 715 configured to receive the collet in a collet lumen 717. In some non-limiting examples, the collet lumen 717 may be smooth. In alternative non-limiting examples, the collet lumen 717 may be textured to better retain the collet 710 within the collet lumen. The socket 715 may also have a cable lumen 719 co-axial with the collet lumen 717 and co-axial as well with the lumen of the collet 712. The socket 715 may comprise a proximal socket flange 720 and a distal socket flange 725 distal to the proximal socket flange. The quick-release mechanism further may comprise a socket seater 730 further comprising a socket lumen configured to receive the socket 715, a socket seater flange 735 disposed between the proximal socket flange 720 and the distal socket flange 725, and a socket seater stub 740. The quick-release mechanism may further comprise a return spring 750 disposed on an exterior surface of the socket seater 730, and a latching arm 745 in contact with the socket seater stub 740. In some non-limiting examples, the latching arm 745 may be configured to exhibit a first state, a second state, and a third state.

The mechanism of action of the quick-release mechanism may depend in part on the relative placement of the various flanges. Thus, as depicted in FIG. 7, the proximal socket flange 720 may extend from an exterior surface of the socket 715, and the distal socket flange 725 may extend from the exterior surface of the socket. Additionally, the socket seater flange 735 may be disposed at a distal end of the socket seater 730 and may protrude at least in part into a space bounded at least in part by the proximal socket flange and the distal socket flange. As a result of this geometry, linear motions of the socket seater 730 may be constrained by the position of the socket 715.

The socket seater 730 may include a socket seater stub 740 that may protrude from the exterior surface of the socket seater and, additionally, may be engaged to move by the latching arm 745. The latching arm 745 may be in contact with a handle at a first end and in contact with a mechanical switch at a second end. The handle may be used by a surgeon to operate the quick-release mechanism. The mechanical switch may exhibit a first stable state, a second stable state, a first transitory state, and a second transitory state. In a non-limiting example, the mechanical switch may be configured to be placed sequentially into the first stable state, the first transitory state, the second stable state, and the second transitory state. As one non-limiting example, the mechanical switch may comprise a pin 755 and a closed-loop track 760, in which the closed-loop track is configured to receive a first end of the pin, and the latching arm 745 is configured to receive a second end of the pin.

Figure 8A:
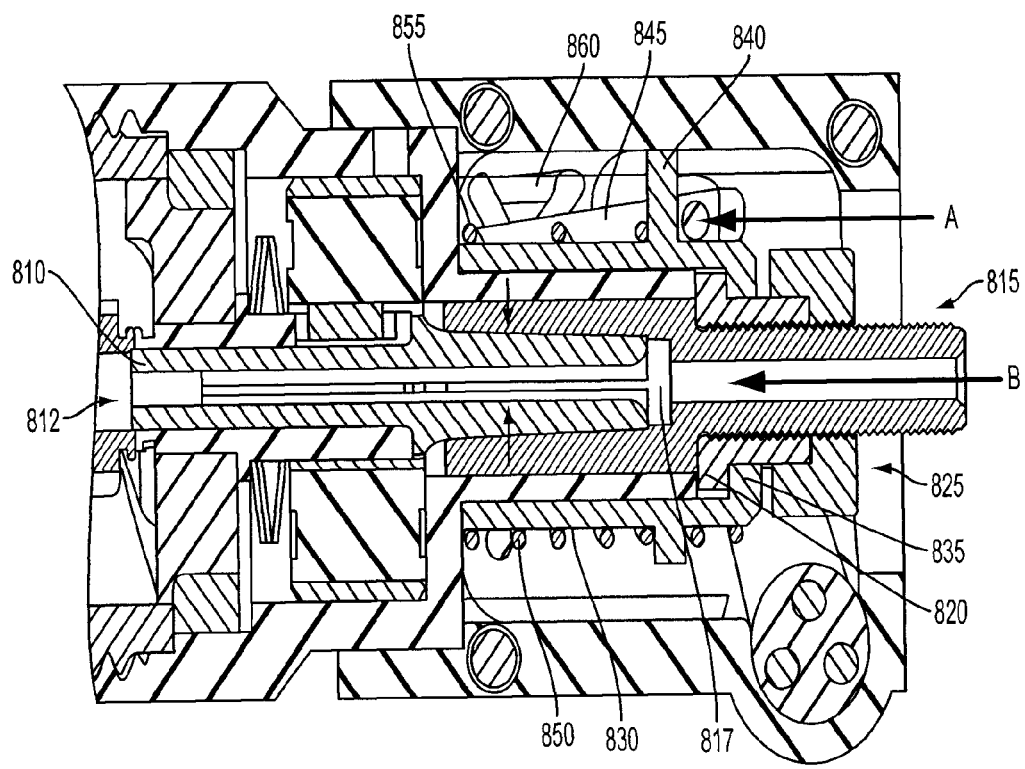
FIGS. 8A-8C depict a mechanism of action of a quick-release mechanism for a Kirschner wire in a cannulated hammer drill attachment according to an embodiment.
Figure 8B:
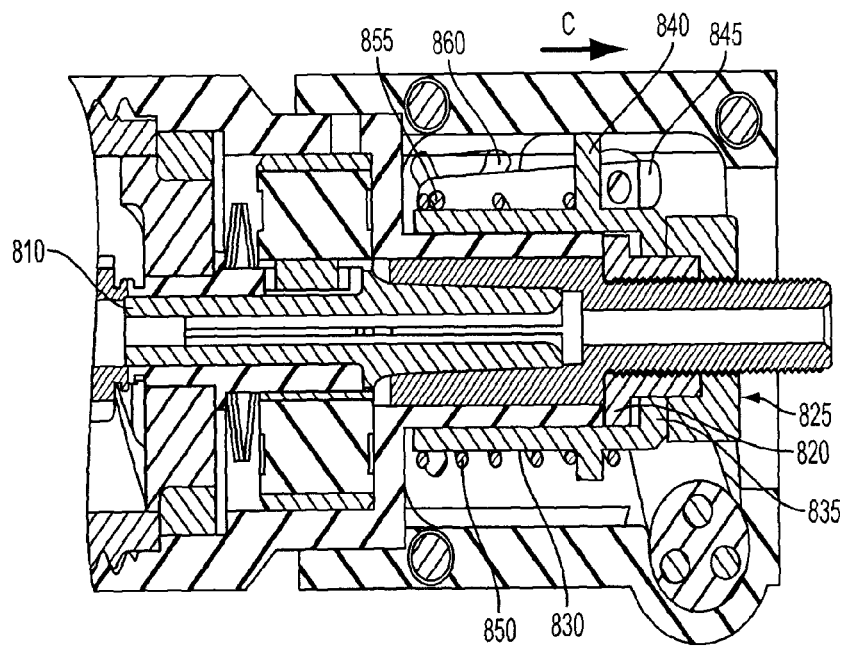
Figure 8C:
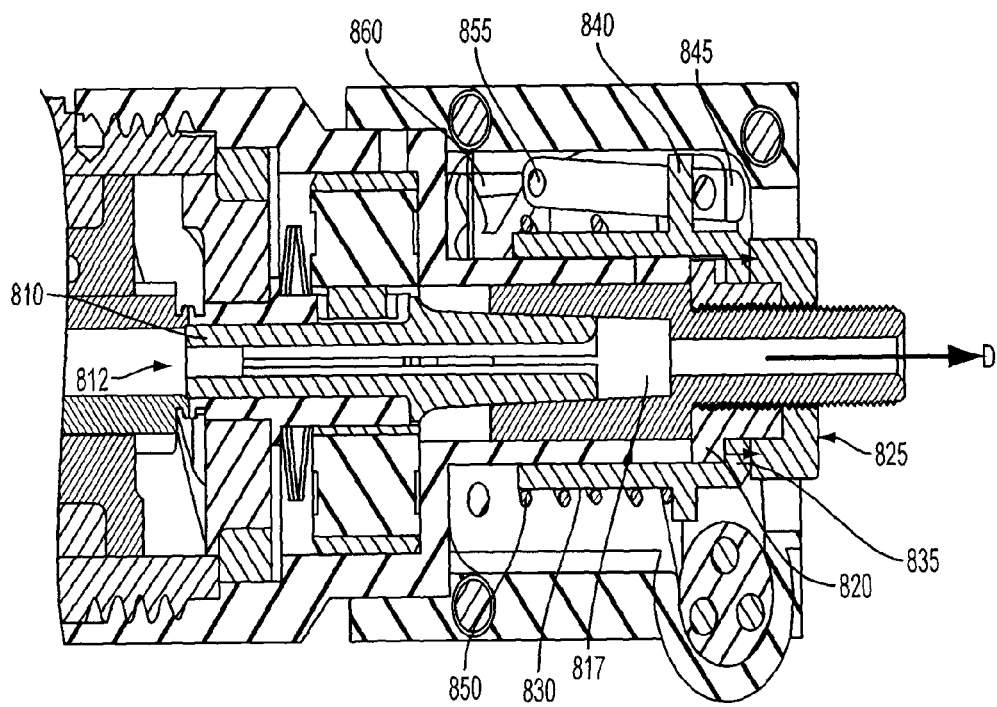

FIG. 7 along with FIGS. 8A-8C illustrates examples of mechanical interactions among the components of a non-limiting embodiment of a quick-release mechanism. Although the components and their interactions are described with respect to FIGS. 7 and 8A-8C, the quick-release mechanism as disclosed herein may be not be limited to components and interactions as depicted solely by these figures.

FIG. 7 depicts a quick release mechanism prior to securing a K-wire. The K-wire may traverse the co-axial lumens including the lumen of the collet 712, the collet lumen 717, and the cable lumen 719. The collet 710 may be disposed at least in part within the socket lumen 717. As depicted in FIG. 7, a K-wire traversing the lumen of the collet 712 and the collet lumen 717 may freely move without being bound by the collet. The latching arm 745 may be positioned by the pin 755 at one end of the closed-loop track 760.

As depicted in FIG. 8A, a force applied to the handle may engage the latching arm 845 to move in a proximal direction, thereby causing the socket seater stub 840 also to move proximally, as indicated by arrow A. The motion of the socket seater stub 840 may cause the socket seater 830 to move similarly in a proximal direction as indicated by arrow B. Additionally, the pin 855 associated with the latching arm 845 may traverse a portion of the closed-loop track 860 to a first transient state. The latching arm 845 may be effectively in the first latching arm state while the pin 855 is in the first pin transitory state. The mechanical configuration depicted in FIG. 8A may portray a first state of the latching arm 845 in which a proximal face of the socket seater flange 835 may contact a distal face of the proximal socket flange 820, thereby transferring a proximal force to the proximal socket flange. The latching arm 845, when placed in the first state, can move the socket seater stub 840 in a proximal direction, thereby moving the socket seater 830 and the socket seater flange 835 in a proximal direction. As the socket seater 830 moves in a proximal direction, the socket seater flange 835 engages the distal face of the proximal socket flange 820 and moves it in a proximal direction as well, thereby pulling the socket 815 onto the collet 810 and securing the exterior surface of the collet against the inner surface of the collet lumen 817. When the collet 810 is thus engaged by the socket 815 in this manner, the collet may collapse by constriction, and thus secure a K-wire traversing the lumen of the collet 812. It may also be noted that the relative positions of the socket 815 and the socket seater 830 as depicted in FIG. 8A may result in compression of the return spring 850.

FIG. 8B depicts the quick-release mechanism after the K-wire has been secured by the collet 810. As depicted in FIG. 8B, after the force has been released from the handle, the latching arm 845 may move in a distal direction under the restoring force of the return spring 850. The pin 855 associated with the latching arm 845 may traverse a portion of the closed-loop track 860 to a first stable state. This pin state may be considered stable in that the pin 855 may remain in this state without the application of force to the handle. The first stable state of the pin 855 may result in placing the latching arm 845 stably in the second latching arm state. As a result, the socket seater stub 840 may move partially in a distal direction under the restorative force of the return spring 850, as indicated by arrow C. The mechanical configuration depicted in FIG. 8B may portray a second state of the latching arm 845 in which the socket seater flange 835 may be positioned between the proximal socket flange 820 and the distal socket flange 825 so that the socket seater flange makes no contact, or only a minimal contact, with the proximal socket flange or with the distal socket flange. As a result, axial percussive force that may be delivered by the drill attachment to the K-wire through the collet 810 may not be impeded by the socket seater 830 or the socket seater flange 835.

The K-wire may be released from the hammer drill attachment by a second application of force to the handle and subsequent release, as depicted in FIG. 8C. As depicted in FIG. 8C, a second force applied to the handle may engage the latching arm 845 to move in a slight proximal direction, thereby causing the socket seater stub 840 also to move slightly proximally. Additionally, the pin 855 associated with the latching arm 845 may traverse a portion of the closed-loop track 860 to a second transient state. In this second transient state, the proximal face of the socket seater flange 835 may contact the distal face of the proximal socket flange 820. With respect to the socket seater flange 835 and proximal socket flange 820, the latching arm 845 may be transiently in the first latching arm state while the pin 855 is in the second pin transitory state. Upon release of the second force against the handle, the latching arm 845 may continue to move in a distal direction under the restoring force of the return spring 850, as indicated by arrow D. The pin 855 associated with the latching arm 845 may traverse a portion of the closed-loop track 860 to a second stable state. This second stable pin state may be considered stable in that the pin 855 may remain in this state without the application of force to the handle. The second stable state of the pin 855 may result in placing the latching arm 845 stably in the third latching arm state. The first stable state of the pin 855 may result in placing the latching arm 845 stably in the second latching arm state. The mechanical configuration depicted in FIG. 8C may portray a third state of the latching arm 845 in which a distal face of the socket seater flange 835 may contact a proximal face of the distal socket flange 825, thereby transferring a distal force (from the return spring 850) to the distal socket flange. The latching arm 845, when placed in the third state, can move the socket seater stub 840 in a distal direction, thereby moving the socket seater 830 and the socket seater flange 835 in a distal direction. As the socket seater 830 moves in a distal direction, the socket seater flange 835 engages the proximal face of the distal socket flange 825 and moves it in a distal direction as well, thereby pulling the socket 815 off the collet 810 and releasing the exterior surface of the collet from the inner surface of the collet lumen 817. When the collet 810 is not engaged by the socket 815 the collet may expand, and thus release the K-wire traversing the lumen of the collet 812. It may also be noted that the relative positions of the socket 815 and the socket seater 830 as depicted in FIG. 8C may result in the return spring 850 expanding to its original dimensions as depicted in FIG. 7.

Figure 9:
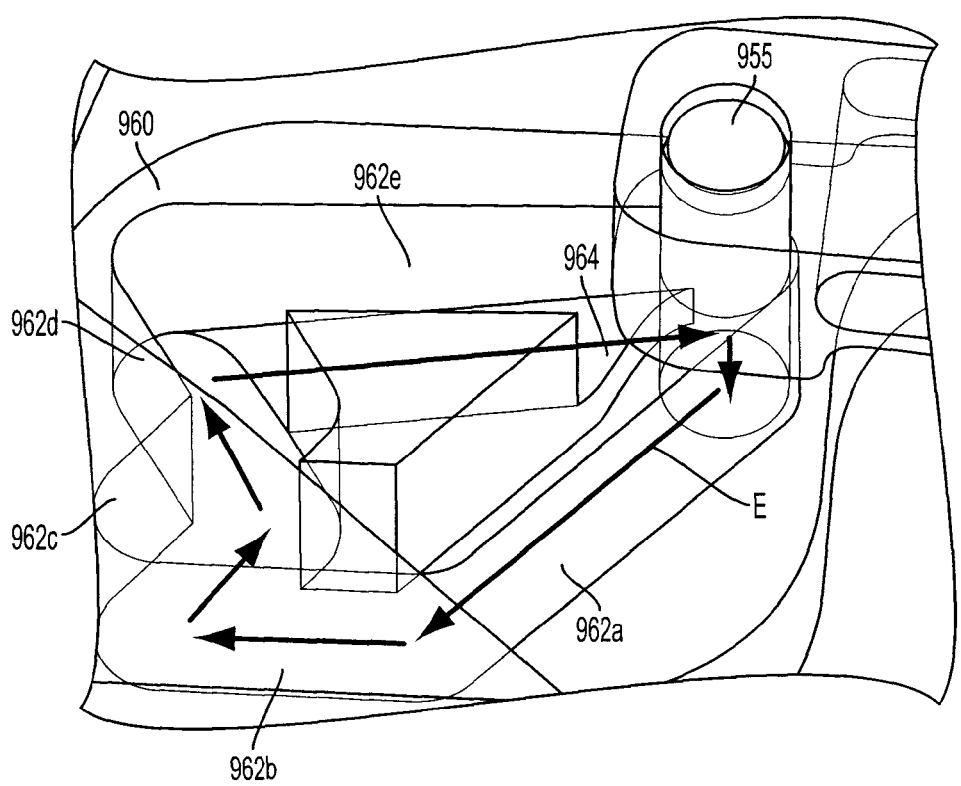
FIG. 9 depicts a close-up of one example of a pin and closed-loop track for a quick-release mechanism for a Kirschner wire in a cannulated hammer drill attachment according to an embodiment.

It may be appreciated that the cycling of the latching arm among the three states may depend on interactions between the pin and the closed-loop track. FIG. 9 depicts an expanded view of one embodiment of the pin and closed loop track. As depicted in FIG. 9, the pin 955 may have one end in contact with the closed-loop track 960 and a second end in contact with the latching arm. The pin 955 may be constrained to travel in a single direction around the closed-loop track 960 as indicated by arrows E. The closed-loop track 960 may comprise a plurality of track segments 962a-e. Each of the track segments 962a-e may be independently chosen from a straight segment (such as 962a, 962b, and 962e) and a curved segment (such as 962c and 962d). In the non-limiting configuration depicted in FIG. 9, at least one of the track segments 962e may comprise a rising ramp on which the pin 955 may move in an orthogonal direction to a plane defined by the track. The pin 955 may be constrained in the closed-loop track 960 by the latching arm. In one non-limiting example, the latching arm may comprise a flexure configured to apply a force to the pin 955 in the orthogonal direction. When the pin 955 is located at the intersection between tracks 962a and 962e, a proximal force applied to the pin by the latching arm can only direct the pin down track 962a because the cut-off 964 of the ramp 962e may not permit the first end of the pin 955 to move along track 962e.

Figure 10:
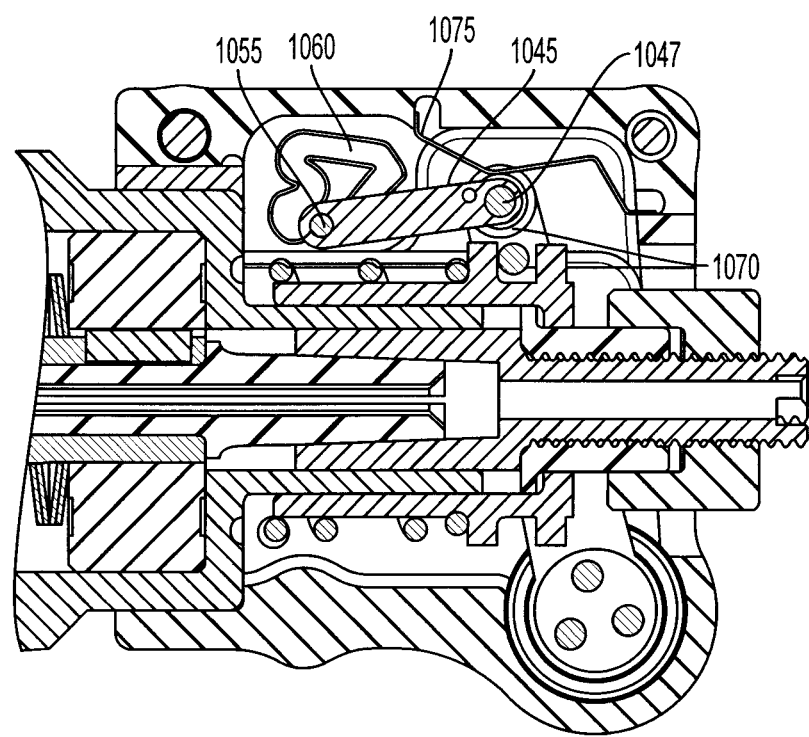
FIG. 10 depicts a close-up of an alternative example of a pin and closed-loop track for a quick-release mechanism for a Kirschner wire in a cannulated hammer drill attachment according to an embodiment.

An alternative example of the mechanical switch is depicted in FIG. 10. As in FIG. 9, FIG. 10 depicts mechanical switch comprising a closed-loop track 1060 and a pin 1055 having a first end disposed in the closed-loop track and a second end in contact with a latching arm 1045. A leaf spring 1075 may be releasably in contact with at least a portion of a surface of the latching arm 1045. Additionally, a torsional return spring 1070 may be disposed about a latching arm axle 1047. The latching arm 1045 may pivot about the latching arm axle 1047 in a clockwise or counter-clockwise manner. As the latching arm 1045 moves to the first latching arm state, the leaf spring 1075 may contact the latching arm, biasing its motion in a counter-clockwise manner through a restoring force, and thereby forcing the latching arm to guide the pin 1055 to its first transitory state. Once the latching arm 1045 is in its first state, the surface of the latching arm may no longer contact the leaf spring 1075. As the pin 1055 transitions to its first stable state, a rotational force from the torsional return spring 1070 may drive the pin to its first stable state. It may be appreciated that the restoring force generated by the leaf spring 1075 may be greater than the rotational force generated by the torsional return spring 1070 to the latching arm through the latching arm axle.

Figure 11:
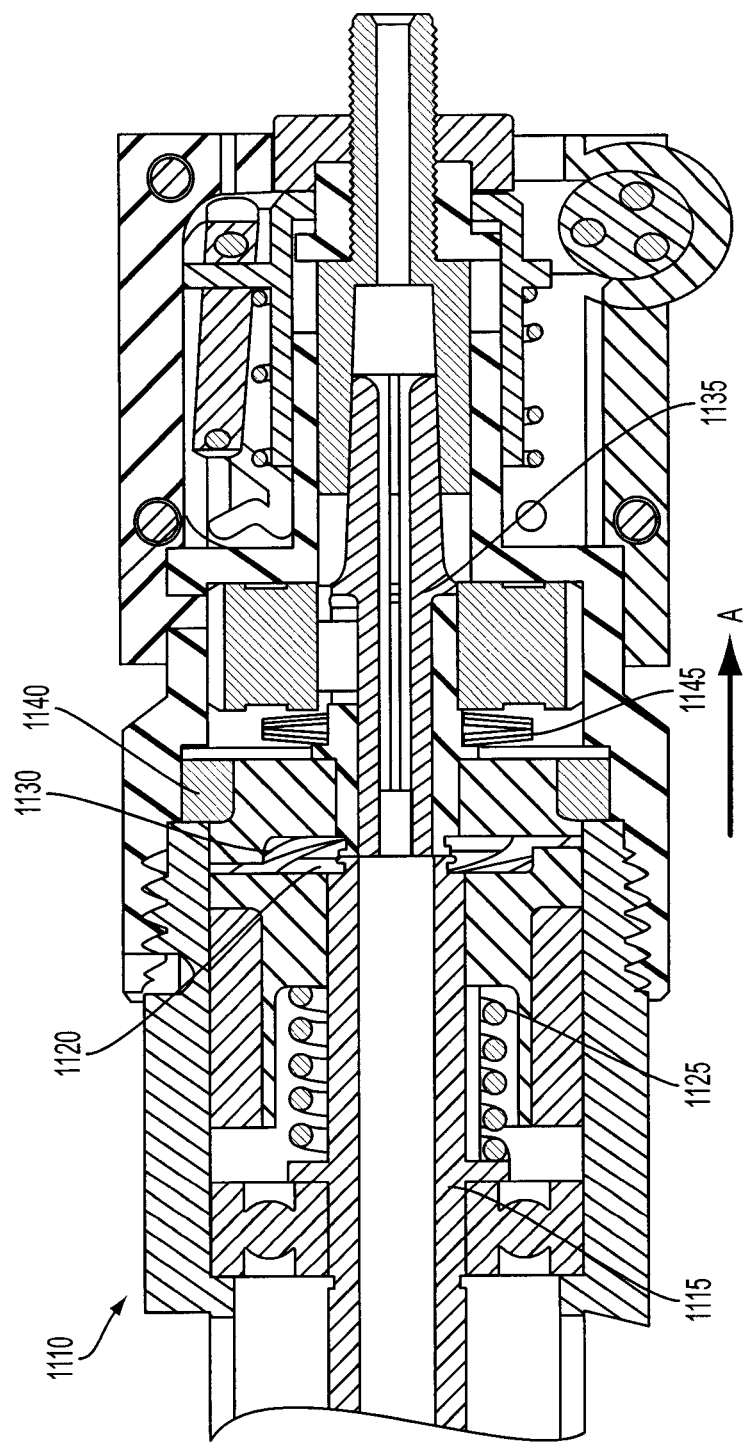
FIG. 11 depicts a transmission mechanism of a cannulated hammer drill attachment according to an embodiment.

The hammer drill attachment may also include a transmission mechanism, as depicted in FIG. 11. The transmission mechanism may comprise a housing 1110, a proximal toothed plate 1120 disposed within the housing and including a body having a distal side comprising a plurality of teeth, and a distal toothed plate 1130 disposed within the housing and including a body having a proximal side comprising a plurality of teeth configurable to engage the plurality of teeth of the proximal toothed plate. The proximal toothed plate 1120 may comprises a number of teeth equal to a number of teeth of the distal toothed plate 1130. In some non-limiting examples, the number of teeth of the proximal toothed plate 1120 and the distal toothed plate 1130 may be about 3 to about 8. Non-limiting examples of the number of plate teeth in the proximal toothed plate 1120 and the distal toothed plate 1130 may be about 3 teeth, about 4 teeth, about 5 teeth, about 6 teeth, about 7 teeth, or about 8 teeth.

The housing 1110 of the transmission mechanism may be configured to axially constrain the distal toothed plate 1130. Each tooth of the proximal toothed plate 1120 and each tooth of the distal toothed plate 1130 may comprise a riser side and a ramp side. Within the transmission mechanism, a rotation of the proximal toothed plate 1120 in a first direction may engage the plurality of teeth of the proximal toothed plate with the plurality of teeth of the distal toothed plate 1130. Alternatively, a rotation of the proximal toothed plate 1120 in a second direction may transiently disengage the plurality of teeth of the proximal toothed plate from the plurality of teeth of the distal toothed plate 1130 and rotationally slide the plurality of teeth of the proximal toothed plate with respect to the plurality of teeth of the distal toothed plate. As the teeth of the proximal toothed plate 1120 rotationally slide past the teeth of the distal toothed plate 1130, the proximal toothed plate may alternatively separate from the distal toothed plate and mechanically engage the distal toothed plate, thereby imparting an axial impact force to the distal toothed plate in a distal direction as indicated by arrow A.

The transmission may further comprise a lengthwise adapter 1115 having a distal end configured to engage the body of the proximal toothed plate 1120 and impart a rotational motion thereto. The lengthwise adapter 1115 may further comprise a proximal end configured to engage a chuck of a drill (not shown). A hammer spring 1125 may be disposed around an outer surface of the lengthwise adapter 1115 and may engage a proximal surface of the proximal toothed plate 1120. The hammer spring 1125 may be configured to compress when the plurality of teeth of the proximal toothed plate 1120 disengage from the plurality of teeth of the distal toothed plate 1130 during a rotation in the second direction. The hammer spring 1125 may additionally be configured to expand when the plurality of teeth of the proximal toothed plate 1120 re-engage the plurality of teeth of the distal toothed plate 1130. During the alternating disengagement and engagement of the teeth of the proximal toothed plate 1120 with the teeth of the distal toothed plate 1130, the hammer spring 1125 may alternately store and deliver a spring force. The spring force may be delivered to the distal toothed plate 1130 as a percussive axial force in the distal direction.

The distal toothed plate 1130 may be configured to axially receive a collet 1135 in a distal central structure thereof. In a non-limiting embodiment, a compliant spring 1145 may be disposed around the distal central structure of the distal toothed plate 1130. The compliant spring 1145 may contact a distal side of the distal toothed plate 1130 on a first compliant spring side, and an inner surface of the housing 1110 on a second compliant spring side. In one non-limiting example, the compliant spring 1145 may comprise a Belleville washer. The compliant spring 1145 may provide a restoring force to the distal toothed plate 1130 as the axial force generated by the hammer spring 1125 is applied. It may be further understood that the compliant spring 1145 may have a spring stiffness greater than that of the hammer spring 1125. However, the hammer spring 1125 may compress over a larger distance than the compliant spring 1145, thereby storing a greater amount of force to deliver the percussive axial force to the collet 1135.

Additionally, the transmission mechanism depicted in FIG. 11 may include additional compliance bearings 1140 mechanically coupled to the distal toothed plate 1130. Such compliance bearings 1140 may serve to decouple the percussive axial force delivered to the distal toothed plate 1130 from the housing 1110.

A drill attachment for a bi-direction drill may incorporate the quick release mechanisms depicted in FIGS. 7-10 along with the transmission mechanism depicted in FIG. 11 and as disclosed above. The drill attachment may include a single housing to contain both the components of the transmission mechanism and the quick-release mechanism. The transmission mechanism may be configured to rotate or apply a percussive distal axial force to a collet that is common to the quick-release mechanism.

A surgical drill kit may include a bi-directional cannulated surgical drill and a drill attachment. The drill attachment may incorporate the quick release mechanisms depicted in FIGS. 7-10 along with the transmission mechanism depicted in FIG. 11 and as disclosed above. The drill attachment may include a single housing to contain both the components of the transmission mechanism and the quick-release mechanism. The transmission mechanism may be configured to rotate or apply a percussive distal axial force to a collet that is common to the quick-release mechanism.

EXAMPLE 1

Cannulated Hammer Drill Attachment

A hammer drill attachment 30 as shown in FIG. 2 and constructed as shown in the exploded view of FIG. 3 has a housing 40 that has an attachment portion 42 which is configured to be attached to a drill, such as drill 10 of FIG. 1. The attachment portion 42 is configured to enable the attachment 30 to be used for various models of drills 10. The attachment 30 has an input shaft 34 that engages with the drive of the drill and an output shaft 35 coaxial with the input shaft. A collet 33 is provided on the output shaft 35 to connect the output shaft with a drill wire. The shafts are cannulated for passage of a surgical drill wire therethrough to enable the attachment to be used with cannulated surgical drills. The attachment 30 is configured with a transmission arrangement that allows the output shaft 35 to rotate only in one direction upon rotation of the input shaft 34 in a first direction. Upon rotation of the input shaft 34 in the opposite direction, the transmission converts the rotation into a hammering action to produce a hammering action at the output shaft 35.

EXAMPLE 2

Surgical Drill Kit

A surgical drill kit may include a cannulated surgical drill such as drill 10 of FIG. 1. A cannulated hammer drill attachment 30 may be included as part of the kit, and various other optional attachment devices may also be included, such as keyless chucks, quick-connect drill attachments, reamers, sagittal saws, and reciprocating saws. In addition to any attachment devices, device accessories may also be included such as rechargeable batteries, saw blades, and drill bits, and may include drill wires, such as various gauges of Kirschner wires 12 of FIG. 1 and/or a drill wire 50 of FIG. 5. Kits may be sold as pre-packaged assortments of contents, or may be custom ordered to create a kit that meets the needs of a particular surgeon.

EXAMPLE 3

Surgery for Repair of Pelvic Fractures

An incision of approximately 3 cm will be made in a patient at a location from which the surgeon wishes to approach the broken bone. Upon exposing the bone, the surgeon will drill a first hole through the outer cortical bone using a surgical drill (such as drill 10 of FIG. 1) equipped with a standard drill chuck and an appropriate drill bit. The hole will be drilled using the forward drill rotation button to drill into the bone. The standard drill chuck will be removed, and a cannulated hammer drill attachment 30 will be affixed to the drill via the attachment portion 42 of the housing 40. A K-wire (50 of FIG. 5) having a diameter of about 1.5 mm and a sharpened tip of about 10 mm disposed at an angle A of about 30° from the axis of the wire will then be inserted through the cannula of the drill and hammer drill attachment.

A fluoroscope will be used to track progress of the wire through the bone. The bent and sharpened tip will be inserted into the drilled hole and directed in a first direction in which it is desired to form a curved hole. The surgeon will press the reverse rotation button and produce a hammering output to drive the tip and wire into the cancellous bone to divert the hole in the first direction. Upon reaching a satisfactory extent of curvature of the hole in the desired first direction and wishing to then proceed in a straight path, the surgeon will rotate the tip 180° from the first direction and hammer drive the wire into the bone approximately another 0.5 cm to 1 cm. The tip will again be rotated 180° back to its original direction and advanced by hammering another approximately 0.5 cm to 1 cm. This back and forth reversal of direction will be repeated until an approximately straight hole of a desired length is achieved. Further curvature, and/or straight path segments will be made as needed in the manner as discussed above to produce a bore within the bone in a desired position for receipt of a fixation anchor therein.

Figures 6A, 6B:
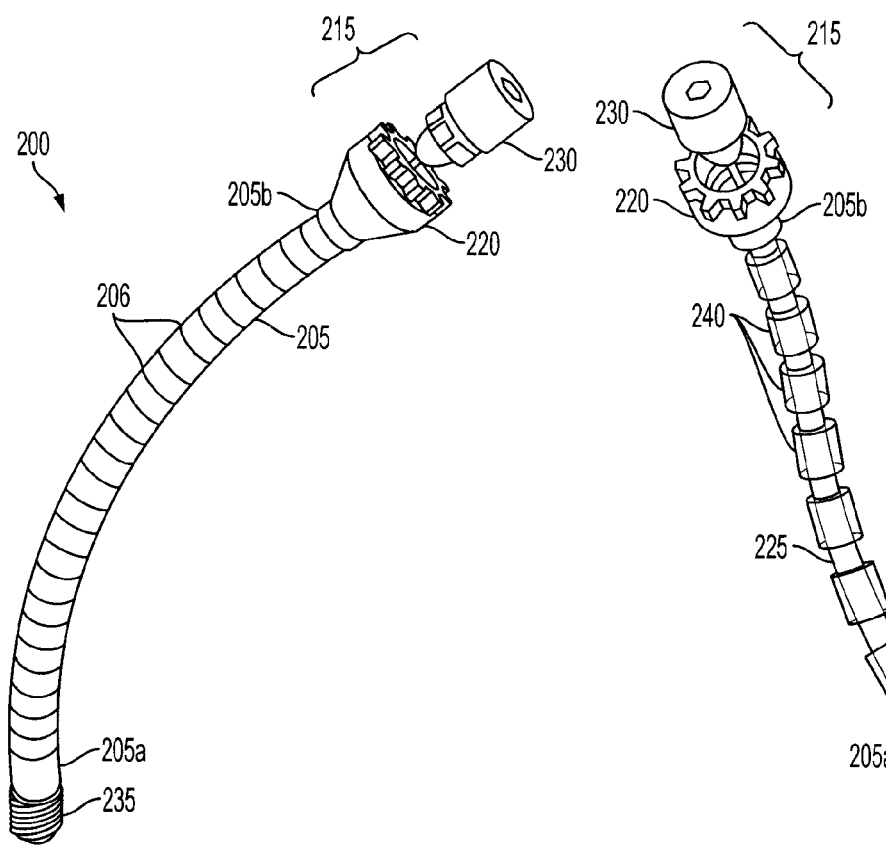
FIG. 6A depicts an exemplary device for fixing a bone according to an embodiment.
FIG. 6B depicts interior portions of the exemplary device of FIG. 6A according to an embodiment.

The K-wire will be left in place, and the curved bore established by the K-wire will be enlarged to about 10 mm diameter by placing a cannulated reamer having a flexible cannulated drive shaft on the K-wire. With visualization provided by the fluoroscope, the reamer will be advanced along the K-wire to approximately the bent tip of the wire. The reamer and wire will be withdrawn leaving an open 10 mm diameter bore through the bone. A fixation device, such as the device 200 as illustrated in FIGS. 6A and 6B, having a corresponding diameter will be inserted into the bore. The device 200 will include a flexible tube 205, a stiffening mechanism 210, an actuator 215, and a threaded screw anchor portion 235.

The anchor portion 235 will be threaded into the bone at the end of the bore to anchor the device 200 in place. The flexible tube 205 will have a distal end 205a and a proximal end 205b. The flexible tube 205 will include a plurality of slits, such as 206, in an outer housing configured to allow the flexible tube to flex. The flexible tube 205 will comprise stainless steel and/or nitinol. The stiffening mechanism 210 will be located within the flexible tube 205 and will be configured to cause the flexible tube to become rigid. The stiffening mechanism 210 will include a plurality of expansion sleeves 240 abutting one another at joints 225. The sleeves 240 will be actuated by rotation of the actuator 215 to expand the sleeves to abut an interior surface of the flexible tube 205 thereby causing the tube to become rigid. A locking assembly 230 will then be engaged with the cap 220 to retain the system in a rigid locked configuration to hold the bone fragments in place.

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A quick-release mechanism for a collet, the mechanism comprising:
   a socket configured to receive the collet in a collet lumen, the socket comprising:
      a proximal socket flange, and
      a distal socket flange distal to the proximal socket flange;
   a socket seater comprising:
      a socket lumen configured to receive the socket,
      a socket seater flange disposed between the proximal socket flange and the distal socket flange, and
      a socket seater stub;
   a return spring disposed on an exterior surface of the socket seater; and
   a latching arm in contact with the socket seater stub, the latching arm having a first state, a second state, and a third state.

2. The mechanism of claim 1, wherein the proximal socket flange extends from an exterior surface of the socket, and wherein the distal socket flange extends from the exterior surface of the socket.

3. The mechanism of claim 1, wherein the socket seater flange is disposed at a distal end of the socket seater and protrudes at least in part into a space bounded at least in part by the proximal socket flange and the distal socket flange.

4. The mechanism of claim 1, wherein the socket seater stub protrudes from the exterior surface of the socket seater.

5. The mechanism of claim 1, wherein the latching arm in the first state is configured to contact a proximal face of the socket seater flange to a distal face of the proximal socket flange, thereby transferring a proximal force to the proximal socket flange, wherein the socket seater flange, when the latching arm is placed in the first state, is configured to move the proximal socket flange in a proximal direction, thereby securing an exterior surface of the collet against an inner surface of the collet lumen; wherein the return spring is compressed when the proximal socket flange is moved in the proximal direction.

6. The mechanism of claim 1, wherein the latching arm in the second state is configured to position the socket seater flange such that the socket seater flange makes no contact with the proximal socket flange or with the distal socket flange.

7. The mechanism of claim 1, wherein the latching arm in the third state is configured to contact a distal face of the socket seater flange to a proximal face of the distal socket flange, thereby transferring a distal force to the distal socket flange, wherein the socket seater flange, when the latching arm is placed in the third state, is configured to move the distal socket flange in a distal direction, thereby releasing an exterior surface of the collet from an inner surface of the collet lumen.

8. The mechanism of claim 1, further comprising:
a handle in contact with the latching arm at a first end of the latching arm; and
a mechanical switch in contact with the latching arm at a second end of the latching arm.

9. The mechanism of claim 8, wherein the mechanical switch having a first stable state, a second stable state, a first transitory state, and a second transitory state.

10. The mechanism of claim 9, wherein the first stable state places the latching arm stably in the second latching arm state, and the second stable state places the latching arm stably in the third latching arm state, and wherein the first transitory state and the second transitory state place the latching arm transiently in the first latching arm state.

11. The mechanism of claim 10, wherein the distal toothed plate is configured to axially receive a collet in a distal central structure thereof.

12. The mechanism of claim 11, further comprising a compliant spring disposed around the distal central structure and contacting a distal side of the distal toothed plate on a first compliant spring side and an inner surface of the housing on a second compliant spring side.

13. The mechanism of claim 8, wherein the mechanical switch comprises a pin and a closed-loop track, wherein the track is configured to receive a first end of the pin, and wherein the latching arm is configured to receive a second end of the pin.

14. The mechanism of claim 13, wherein the closed-loop track comprises a plurality of track segments, each of the plurality of track segments independently chosen from a straight segment and a curved segment, wherein at least one of the plurality of track segments comprises a rising ramp on which the pin is configured to move in an orthogonal direction to a plane defined by the closed-loop track.

15. The mechanism of claim 13, further comprising a torsional return spring in contact with a latching arm axle configured to apply a rotational force to the latching arm, and further comprising a leaf spring releasably in contact with at least a portion of a surface of the latching arm and configured to apply a restoring force to the latching arm, wherein the restoring force is greater than the rotational force applied by the torsional return spring to the latching arm through the latching arm axle.

16. The mechanism of claim 1, wherein the socket further comprises a cable lumen co-axial with the collet lumen.

17. A transmission mechanism, comprising:
a housing,
a proximal toothed plate disposed within the housing and comprising a body having a distal side comprising a plurality of teeth;
a distal toothed plate disposed within the housing and comprising a body having a proximal side comprising a plurality of teeth configurable to engage the plurality of teeth of the proximal toothed plate, wherein:
the housing axially constrains the distal toothed plate,
each tooth of the proximal toothed plate and each tooth of the distal toothed plate comprises a riser side and a ramp side,
a rotation of the proximal toothed plate in a first direction engages the plurality of teeth of the proximal toothed plate with the plurality of teeth of the distal toothed plate, thereby imparting a rotational force to the distal toothed plate, and
a rotation of the proximal toothed plate in a second direction disengages the plurality of teeth of the proximal toothed plate from the plurality of teeth of the distal toothed plate and rotationally slides the plurality of teeth of the proximal toothed plate with respect to the plurality of teeth of the distal toothed plate, thereby imparting an axial impact force to the distal toothed plate,
a lengthwise adapter having a distal end configured to engage the proximal toothed plate body and impart a rotational motion thereto, a proximal end configured to engage a chuck of a drill, and
a hammer spring disposed around an outer surface of the lengthwise adapter and engaging a proximal surface of the proximal toothed plate, the hammer spring being configured to compress when the proximal toothed plate disengages the plurality of teeth of the proximal toothed plate from the plurality of teeth of the distal toothed plate during a rotation in the second direction, and configured to expand to deliver a percussive axial force to the distal toothed plate when the plurality of teeth of the proximal toothed plate re-engages the plurality of teeth of the distal toothed plate.

18. A drill attachment for a bi-directional drill, the attachment comprising:
a housing;
a lengthwise adapter comprising a proximal end configured to engage a chuck of the bi-directional drill;
a transmission mechanism configured to engage a distal end of the lengthwise adapter, comprising:
a proximal toothed plate disposed within the housing and comprising a body having a distal side thereof comprising a plurality of teeth, and
a distal toothed plate disposed within and axially constrained by the housing and comprising a body having a proximal side comprising a plurality of teeth configurable to engage the plurality of teeth of the proximal toothed plate, wherein each tooth of the proximal toothed plate and each tooth of the distal toothed plate comprises a riser side and a ramp side, wherein a rotation of the proximal toothed plate in a first direction engages the plurality of teeth of the proximal toothed plate with the plurality of teeth of the distal toothed plate, thereby imparting a rotational force to the distal toothed plate, and wherein a rotation of the proximal toothed plate in a second direction disengages the plurality of teeth of the proximal toothed plate from the plurality of teeth of the distal toothed plate and rotationally slides the plurality of teeth of the proximal toothed plate with respect to the plurality of teeth of the distal toothed plate, thereby imparting an axial impact force to the distal toothed plate;

a collet contacting a distal portion of the distal toothed plate; and a quick-release mechanism for the collet comprising,
  a socket configured to receive the collet in a collet lumen, the socket comprising:
    a proximal socket flange, and
    a distal socket flange distal to the proximal socket flange;
  a socket seater comprising:
    a socket lumen configured to receive the socket,
    a socket seater flange disposed between the proximal socket flange and the distal socket flange, and
    a socket seater stub;
  a return spring disposed on an exterior surface of the socket seater; and
  a latching arm in contact with the socket seater stub, the latching arm having a first state, a second state, and a third state.

\* \* \* \* \*